United States Patent [19]

Gordon

[11] Patent Number: 4,662,359

[45] Date of Patent: May 5, 1987

[54] USE OF MAGNETIC SUSCEPTIBILITY PROBES IN THE TREATMENT OF CANCER

[75] Inventor: Robert T. Gordon, 4936 West Estes, Skokie, Ill. 60077

[73] Assignee: Robert T. Gordon, Skokie, Ill.

[21] Appl. No.: 535,390

[22] Filed: Sep. 23, 1983

Related U.S. Application Data

[63] Continuation-in-part of Ser. No. 522,941, Aug. 12, 1983, abandoned.

[51] Int. Cl.⁴ ............................................. A61N 43/00
[52] U.S. Cl. ...................................... 128/1.1; 128/1.3; 128/399
[58] Field of Search .................. 128/1.1, 1.3, 1.5, 399, 128/804

[56] References Cited

U.S. PATENT DOCUMENTS

| | | | |
|---|---|---|---|
| 4,106,488 | 8/1978 | Gordon | 128/1.1 |
| 4,303,636 | 12/1981 | Gordon | 128/1.1 |
| 4,323,056 | 4/1982 | Borrelli et al. | 128/1.3 |
| 4,345,588 | 8/1982 | Widder et al. | 128/1.3 |

Primary Examiner—Edward M. Coven
Attorney, Agent, or Firm—Scully, Scott, Murphy & Presser

[57] ABSTRACT

Described is a process for the treatment of cancer in at least one region of host organism containing cancer cells and normal cells without substantially damaging living normal cells comprising:

providing to a host organism minute particles capable of being inductively heated and of size capable of being absorbed into cancer cells, determining, after a period of metabolic time, the magnetic susceptibility of the particles with said region, subjecting the organism to an alternating electromagnetic field to inductively heat said particles at that point in metabolic time when the maximum difference in magnetic susceptibility between the cancer cell and normal cells within said region occurs, and continuing the inductive heating of said particles to attain an increase in intracellular temperature to selectively kill the cancer cells.

15 Claims, 2 Drawing Figures

USE OF MAGNETIC SUSCEPTIBILITY PROBES IN THE TREATMENT OF CANCER

CROSS REFERENCE TO RELATED APPLICATION

This application a continuation-in-part of copending application U.S. Ser. No. 522,941, filed August 12, 1983. now abandoned

Field of the Invention

This invention relates to the field of cancer treatment. More specifically the invention relates to an improvement in the timing of and the application of a cancer treatment mode.

BACKGROUND OF THE INVENTION

A safe and effective cancer treatment has been the goal of investigators for a substantial period of time. Such a technique, to be successful in the destruction of the cancer cells in situ, must be selective in effect upon the cancer cells and produce no irreversible damage to the normal cells. In sum, cancer treatment must selectively differentiate cancer cells from normal cells and must selectively weaken or kill the cancer cells without affecting the normal cells.

It has been known that there are certain physical differences that exist between cancer cells and normal cells. One primary physical difference that exists is in the temperature differential characteristics between the cancer cells and the normal cells. Cancer cells, because of their higher rates of metabolism, have higher resting temperatures compared to normal cells. The normal resting temperature of the cancer cell is known to be 37.5° Centigrade, while that of the normal cell is 37° Centigrade. Another physical characteristic that differentiates the cancer cells from the normal cells is that cancer cells die at lower temperatures than do normal cells. The temperature at which a normal cell will be killed and thereby irreversibly will be unable to perform normal cell functions is a temperature of 46.5° Centigrade, on the average. The cancer cell, in contrast, will be killed at the lower temperature of 45.5° Centigrade. The temperature elevation increment necessary to cause death in the cancer cell is determined to be at least approximately 8.0° Centigrade, while the normal cell can withstand a temperature increase of at least 9.5° Centigrade.

Based upon the foregoing, a cancer treatment method has been disclosed by the applicant in his U.S. Pat. No. 4,106,488 (the contents of which are incorporated herein by reference) which involves inducing the selective 'death' of cancer cells in a host organism by introducing minute paramagnetic, diamagnetic or ferromagnetic particles to the organism intravenously, and inductively heating the phagocytized particles, utilizing a helical coil surrounding the host and a high frequency alternating electromagnetic field provided by an electronic oscillator, the heating being effected to raise the intracellular temperature of affected cells sufficiently to cause cell death. The treatment relies inter alia upon certain known differences in normal and abnormal cells, in particular the enhanced ability of cancer cells to phagocytize particulate material, and their lower temperature threshold for necrosis as detailed above.

This treatment has been found effective in the selective removal, without surgery, of primary tumors in host organisms, including spontaneously generated tumors recognized to be more difficult objects of therapy. The method offers particular promise in the case of metastatic cancer where the metastatic sites, are inoperable and/or poorly dealt with through chemotherapy, since the Gordon treatment is effected from without the host and may be applied to any region without significant deleterious effect on surrounding normal tissue Now it has nevertheless been necessary, in further studies, to refine several aspects of the treatment protocol as disclosed in U.S. Pat. No. 4,106,488 to accomplish the particularized goal for an individual treatment with greater certitude, accuracy and flexibility. The implementation of this improved treatment method in part utilizes inventive aspects which are the subject of other applications for U.S. Letters Patent by the same inventor as recited hereinafter. For example, a fuller understanding of the technology underlying the Gordon treatment reveals the operation of subtle mechanisms which can themselves become a contributing factor in the course of treatment. Thus, the generation of intracellular substances such as interferon may be stimulated or enhanced during, or as a result of treatment, as disclosed in copending and commonly assigned application Ser. No. 418,298 of the same inventor, incorporated herein by reference.

SUMMARY OF THE INVENTION

The present invention resides principally in a process for treating a host organism including a cell population constituting an invasive abnormality comprising introducing within the host phagocytizable particles capable of being inductively heated in response to an imposed high frequency alternating electromagnetic field where the time of treatment (to effect said inductive heating) is correlated with the maximum responsiveness of particles in the tissue, the object of immediate treatment, as measured by the magnetic susceptibility of the intracellularly localized particles within such tissue. The invention is grounded in the recognition that as various substances are metabolized within a cell, their magnetic characteristics, such as magnetic susceptibility vary.

In particular, the present invention relates to a process for the treatment of cancer in at least one region of host organism containing cancer cells and normal cells without substantially damaging living normal cells comprising:

providing to a host organism minute particles capable of being inductively heated and of a size capable of being absorbed into cancer cells, determining, after a period of metabolic time, the magnetic susceptibility of the particles with said region, subjecting the organism to an alternating electromagnetic field to inductively heat said particles at that point in metabolic time when the maximum difference in magnetic susceptibility between the cancer cell and normal cells within said region occurs, and continuing the inductive heating of said particles to attain an increase in intracellular temperature to selectively kill the cancer cells.

In a further embodiment the subject invention provides a process for the treatment of cancer in at least one region of a host organism containing cancer cells and normal cells without substantially damaging living normal cells comprising: providing to the host organism minute encapsultated tumoricidal material, said encapsulating material capable of being removed upon entering the cancer cell, determining after a period of metabolic time, the magnetic susceptibility of the particles with said region, subjecting the organism to an alternating, oscillating or pulsed electromagnetic field at that point in metabolic time when the maximum difference is magnetic susceptibility between the cancer cells and normal cells occurs thereby removing said encapsulating material and releasing said tumoricidal material within the cancer cells.

According to this embodiment, the release of the tumoricidal material is effected by melting or vibrating the encapsulating material thereby releasing said tumoricidal material. Particularly useful tumoricidal material includes antibodies, radioactive isotopes, and chemotherapeutic agents such as 5-flurouracil, nitrogen mustard, actinomycin D, methotrexate, cytoxan and vincristine.

DETAILED DESCRIPTION OF THE INVENTION

Figure 1A:
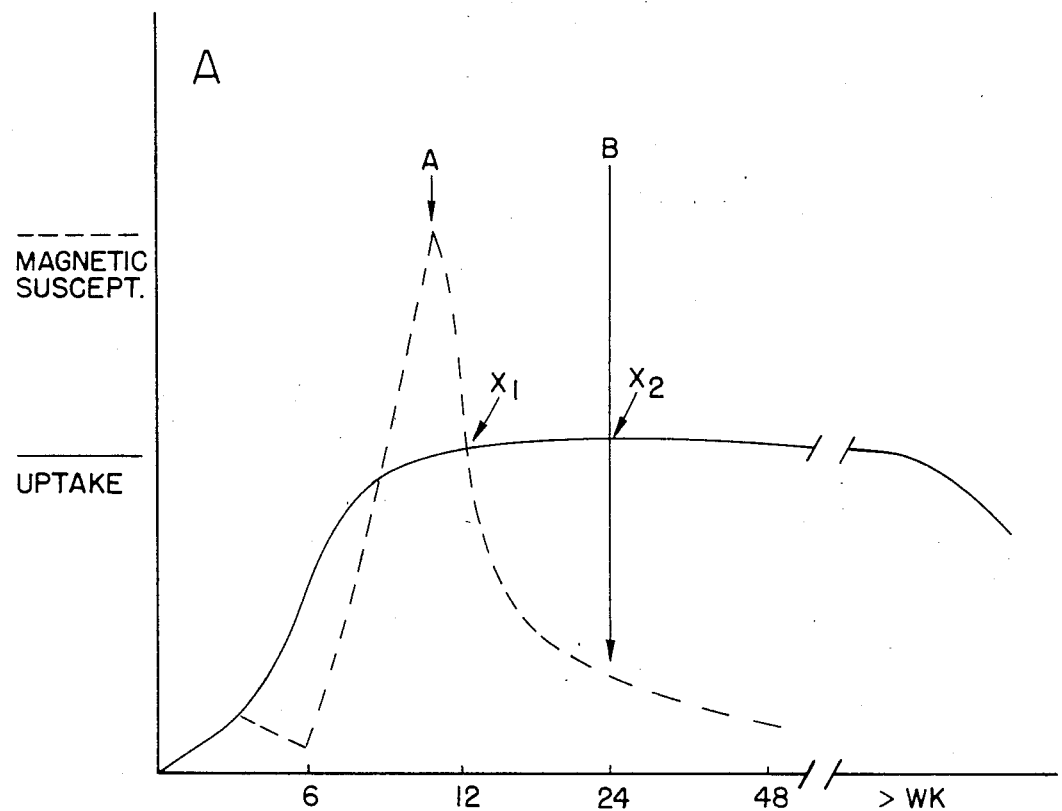
FIG. 1A illustrates the relationship of magnetic susceptibility to particle uptake with time.

The use of magnetic susceptibility as a particle probe affords the advantage of basing the treatment level and timing upon a functional magnetic parameter directly related to inductive heating rather than upon only a potentially functional parameter, i.e., the mere physical presence of the particles. The use of magnetic susceptibility as a particle probe at lower energy levels also affords a more sensitive tool because the magnetic susceptibility is responsive to the interface between the particles and their environment.

As a result, the point at which normal and abnormal cells exhibit the greatest disparity in effective particle population in the region probed can be pinpointed accurately, establishing the optimum period for treatment relative to maximum preservation of the normal cell population with selective necrosis of the greatest number of abnormal cells.

Although the magnetic characteristic of magnetic susceptibility has been selected for detailed discussion herein. The invention also contemplates the use of the magnetic characteristics such as magnetic permeability, or magnetic moments when sensed with the appropriate sensing devices.

In the sensing phase, magnetic susceptibility is used diagnostically, over a period of metabolic time, as described and claimed in copending and commonly assigned application Ser. No. 468,644 of the same inventive entity, incorporated herein by reference. Thus in the instant application of magnetic susceptibility the particles are periodically monitored to provide for the determination of that point, in sensed metabolic time, at which selective localization and optimal susceptibility of the particles within certain tissues, organs, or even within individual cells has been achieved. Taken with other indicia, it is possible then to establish an optimum treatment period, again by referencing the maximum particle responsiveness in the treatment region.

Magnetic susceptibility has also been used heretofore in connection with the Gordon treatment, as disclosed in U.S. Pat. No. 4,163,683, where magnetic susceptibility measurements are correlated with temperature (an interdependent variable) in accomplishing the related induction heating step controllably. There is no recognition, however, that the values for magnetic susceptibility, independent of the induction heating step or the imposition of an electromagnetic field can be usefully correlated (to maximization of particle concentration) with time to optimize treatment effectiveness, as demonstrated herein.

Thus, in accordance with the present invention, a developing plot of magnetic susceptibility of the region of the host organism sensed (by sensitive magnetic sensing equipment such as a vibrating magnetometer, a squid magnetometer or a fluxgate magnetometer) with elapsed time is examined (and if computer assisted, the plot is projected employing an appropriate algorithm), and the one or more maxima (representing maximum relative susceptibility of particles in abnormal vs. normal tissue) are selected for application of the induction heating step. Such sensing may be accomplished without application of the electromagnetic field, or if the treatment capability is concurrently applied, temperature effects if any are factored out of the readings, and resultant plots.

Diagnostic mapping as originally contemplated involved a constant low power trace, and a determination of particle location and concentration by differential comparison of mappings taken over a time interval. Unfortunately, such an approach tends to reflect events, specifically the concentration of particles, which have already occurred. By definition, the optimum treatment time cannot be ascertained in this manner.

To further illustrate the attendant advantage of the subject invention reference is made to FIG. 1. FIG. 1A depicts the relationship between magnetic susceptibility and particle uptake in cells. The magnetic susceptibility data was extracted from copending application U.S. Ser. No. 468,644 wherein the magnetic susceptibility represents a measurement of the induced magnetic moment in relation to the magnetic field strength. The uptake curve is inferred from the analysis of histological examination of tissue slices, the photomicrographs of which indicate the presence of particles for periods of weeks after injection.

Figure 1B:
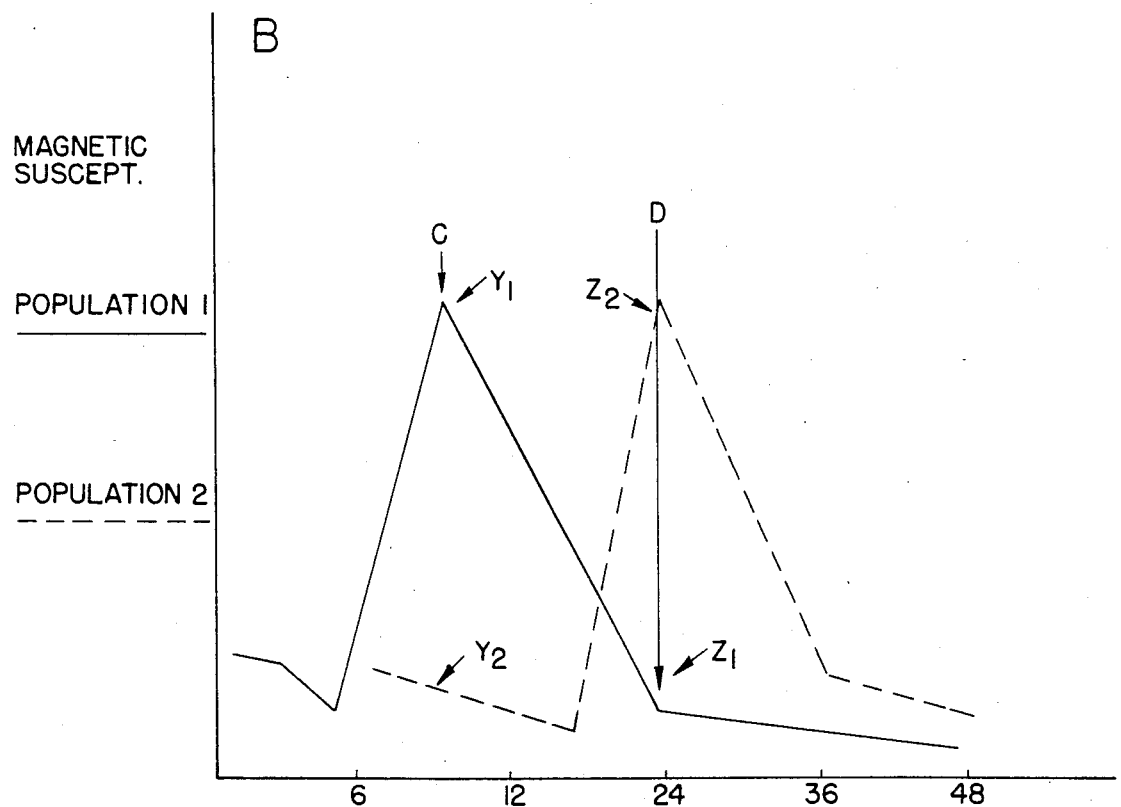
FIG. 1B illustrates the difference in magnetic susceptibility between two hypothetical cell populations.

It is clear that subjecting an organism to treatment at point A is much preferable than at point B since treatment during a period of high magnetic susceptibility allows for a more efficient response to alternating magnetic field. If, however, particle uptake were to be used as the treatment criterion point $X_1$ and $X_2$ would be given equal consideration as representing a period of maximum particle uptake. The application of equal amounts of energy at point $X_1$ and $X_2$ would result in a far less effective treatment due to the less than optimal state of the particles at point $X_2$ FIG. 1B illustrates another aspect of the instant invention. FIG. 1B depicts the relative magnetic susceptibility between cell populations. The difference in timing could result from a difference in particle uptake, a difference in the rate of metabolism of the particles or a combination thereof. It is clear that treatment at point C would likely affect the first population to a greater extent then the second, compare points $Y_1$ and $Y_2$. Conversely treatment at point D would likely have an opposite effect (compare point $Z_2$ with $Z_1$).

As with any treatment, the first consideration is the condition of the host organism, or patient, in all of the medically recognized respects, thus providing sufficient information to permit the requisite targeting of a selective treatment mode. In the case of invasive abnormalities and especially cancer, it is naturally desirable to locate the primary sites, or the metastatic site for further treatment, and this may be accomplished as aforesaid, by using the Gordon methodology itself, as described in fuller detail hereinbelow, employed in a low energy detection mode.

In order to provide a suitable frame of reference in which to fully understand the refinements disclosed herein, the treatment regimen may be construed to be comprised of pre-treatment, and post-treatment phases and/or considerations. It is recognized, of course, that inherently an operation in one phase will necessarily affect other phases since the regimen is highly integrated.

The choice of particle type can be highly significant to effective treatment, particularly where subcellular localization or other subtle differentiations in metabolic activity, for example, are conveniently utilized to maximize particle uptake in the region selected for the Gordon treatment. Suitable particles and exemplifications of selection parameters are disclosed and examined in co-pending and commonly assigned application Ser. No. 464,870 of the same inventor, incorporated herein by reference. Although metabolizable particles are especially useful, metabolically inert particles which are still able to be magnetically mapped, may also be usefully employed.

Furthermore, the pre-treatment stage can be managed in such manner as to maximize particle uptake. In particular, a metal deficient diet will aid in assimilation, transport and localization of a particle based upon the needed metal. In the same sense, the choice of particle suspension can be important, e.g., selection of ionic character or level, or pH in the preferred colloidal vehicle.

Once the particles have been introduced into the host organism, they are in a dynamic state due to the action of the extracellular, and intracellular environment to which they are exposed. In this latter respect, it will be understood that from assimilation through execretory function, body mechanisms related to the character of the particles' chemical and physical characteristics (including elemental form, ionic character, size, shape, reactivity, biofunction, etc.) as well as the particles' participation in cellular-function or migration through related metabolic pathways, operate to provide a certain traceable sequence of particle locations with the passage of time. Such a determination of the location and metabolic state of the particles may be made at energy levels sufficient to sense the presence of the particles but insufficient to effect any meaningful induction heating.

In a particularly advantageous aspect of the methodology, the chemical constitution of the particle embodies a radioisotope, antibodies or chemotherapeutic agents or metabolic precursors thereof in free or encapsulated forms intended for delivery and application in the region also to be treated by induction heating, in order to achieve a certain synergy of action.

In accordance with a preferred embodiment of the invention the characteristics of the imposed field are selectively varied, in contrast to the essentially invariant alternating electromagnetic field previously disclosed. Thus, the wave shape may be modified for a given treatment or varied within a given treatment in such a manner to change frequency or amplitude. The field may even be maintained in a static form and then alternated, in one sequence or an iterated series thereof.

It has been appreciated that the imposition of a localized, static field may be used to enhance particle uptake as well as increase the efficiency of energy absorption form the alternating field applied during the treatment phase.

Conveniently, where a static field is imposed, the magnetometer measurements are made periodically, during scheduled interruptions in the generation of the field until the projected plot of magnetic susceptibility vs. time approaches a maximum for the targeted treatment region, whereafter the field characteristics are modified for the selected treatment, e.g., to a higher energy high frequency alternating electromagnetic field. It will of course be understood that magnetic susceptibility measurements may also be made during interruptions in the high frequency field in the treatment phase.

In another embodiment the application of the localized static field may occur concurrently with the application of an alternating, oscillating or pulsed electromagnetic field. That is to say, the localized static field may be susperimposed on the host organism while the alternating, oscillating or pulsed field is also being applied.

Such measurements may be used to provide correlations with induced treatment temperatures, as described in Gordon U.S. Pat. No. 4,136,683 although this does not constitute part of the present invention, per se.

Reference to magnetic susceptibility plotting mediate the treatment phase may of course be augmented or for that matter supplanted by plots over an extended time, particularly where assimilation and localization of the particles requires such a time frame, in a metabolic sense, or for change of ionic condition with diet or fluid intake, or development of modified hormonal levels, etc.

When the inventive treatment is in conjuction with chemotherapeutic agents, there are attendant advantages in correlating the introduction of the chemotherapeutic agent to the treatment region (whether introduced by ingestion, etc.) to the induction heating such that the actions of the agent is coordinated with the effect of such treatment.

Thus, in particular cases, the chemotherapeutic effect may precede or follow the induction heating to augment the treatment. It will be appreciated that the chemotherapeutic agent may form part of the constitution of the particles used for the induction heating such that the active element is released at a tumor site. Such particles are disclosed in the application Ser. No. 464,870 referred to above.

Post-treatment may involve the reverse phenomenon, as described in the pre-treatment phase where the provision or body fluids, or diet is employed to deliver substitute materials aiding in the excretion of the particles supplied for treatment.

The application of chelating therapy to facilitate the sequestering and ultimate excretion of the particles is not ruled out by the above procedure, although such therapy is not considered to be a part of the subject invention per se.

Reference herein to tissue, organ or cell population is intended in its most embracive and comprehensive sense, referring in general to the region of the host organism affected by the invasive abnormality, or the treatment region, as the context requires.

To further illustrate the operation of the subject procedure, the following treatment scenario is provided.

The subject receives an intravenous injection of colloidally suspended inductible heatable particles, such as iron porphyrin (FeTPPS$_4$) at a dosage of 10 mg/kg. Magnetic susceptibility mapping measurements are made periodically to follow the distribution of the particles within the body. The subject is then exposed to a static magnetic field in the range of 500 gauss to 80 kilogauss, the exact exposure being determined by the practitioner. This exposure acts to enhance uptake of the particles in the desired treatment area as well as to increase the efficiency of subsequent energy absorption. Measurements of the magnetic susceptibility may be made and recorded utilizing magnetometry equipment such as a "Squid" or flux-gate type. When the magnetic susceptibility of the particles in the treatment area relative to surrounding tissue is at a peak, the subject is exposed to an alternating electromagnetic field as described in applicants U.S. Patent No. 4,106,488. The static magnetic field of 500 gauss to 80 kilogauss is preferably applied immediately prior to the application of the alternating electromagnetic field to optimize energy delivery to the particles since the acquisition of magnetic moment and alignment help to enhance the effect of the alternating electromagnetic field. Although not wishing to be bound by the following, the applicant suggests that the enhancement may be the result of:

(a) the creation of an environment more favorable for the intracellular absorption of particles, and/or (b) the orientation of the particles with configurarions for better subsequent absorption of electromagnetic energy, and/or (c) the creation of an environment fostering intracellular migration of particles towards the nucleus thereby increasing the efficacy of treatment, and/or (d) the fostering of the clustering of particles which result in greater subsequent energy absorption.

Regardless of the explanation proffered, the subject is treated when the magnetic susceptibility is greatest in the treatment area relative to other surrounding tissues and when the particles are in the optimum relative electromagnetic energy absorption state to be inductively heated. Hence the target area will be selectively treated while the surrounding tissue will be subjected to the least amount of damage.

Chelating agents such as desferroxamine may be utilized to enhance secretion of the particles after treatment. Chloroquine or other similar agents may also aid in iron secretion as well.

Although the effective electromagnetic fields referred to herein have been characterized as alternating electromagnetic fields, there is no evidence which would preclude the use of electromagnetic fields of the oscillating or pulsed type and such fields are contemplated by the subject invention.

Thus, the subject invention not only provides an effective method for monitoring the treatment phase so as to allow for treatment techniques based upon limited increases in temperature (i.e., rises in temperature of 9.5° C), but also provides for an additional treatment technique. In this further embodiment, since the subject invention provides a means for specific particle distribution and a sensing of the responsiveness to the various treatment fields, high temperature treatment modalities are also possible. The 9.5° C. limitation as discussed supra is, of course, predicated on the case situation in which particle distribution, magnetic state, and orientation were equal in all cancer cells and normal cells under the treatment conditions. However, employing the improved methods of the subject invention thereby affecting specific particle distribution, orientation, differential magnetic susceptibility, timing and other parameters described herein, between the cancer cells and the normal cells within the target area, increases in the intracellular temperature up to 100° C. are possible without substantially damaging the surrounding normal cells.

Irreversible cell death and biological alterations are induced by the energy input to the particle and thereupon to the interior of the cancer cell. Thus the same energy input may be accomplished by application over a long period of time with a consistant small temperature rise (8° to 9° C. for 10-20 minutes) or when the same total amount of energy is applied over a short period of time a higher temperature results (100° C. for a few seconds).

Obviously, timing and energy parameters may be adjusted to provide a spectrum of intracellular temperature which may be utilized depending upon the treatment appropriate in specific cases.

What is claimed is:

1. A process for the treatment of cancer in at least one region of a host organism containing cancer cells and normal cells without substantially damaging living normal cells comprising:

providing to a host organism minute particles capable of being inductively heated and of a size capable of being absorbed into cancer cells, determining, after a period of metabolic time, the magnetic susceptibility of the particles within said region, subjecting the organism to an alternating, oscillating or pulsed electromagnetic field to inductively heat said particles at that point in metabolic time when the maximum difference in magnetic susceptibility between the cancer cell and normal cell within said region occurs, and continuing the induction heating of said particles to attain an increase in intracellular temperature to selectively kill the cancer cells.

2. The process of claim 1 including the further step of applying a localized, static field to aid in the intracellular uptake and the energy-absorption responsiveness of said particles, said field being applied after the provision of the particles to the host organism but prior to or during the application of said electromagentic field.

3. The process of claim 2 wherein the strength of static field is between about 500 gauss to about 80 kilogauss.

4. The process according to claim 1 wherein said induction heating is continued to attain an increase in intracellular temperature of said cancer cells of between 8° C. and 100° C. to kill said cancer cells.

5. The process according to claim 1 wherein said induction heating is continued to attain an increase in intracellular temperature of at least 8.0° Centigrade and not greater than 9.5° Centigrade to kill said cancer cells.

6. A process for treating a host organism including a cell population constituting an invasive abnormality comprising introducing within the host phagocytizable particles capable of being inductively heated in response to an imposed high frequency alternating electromagnetic field inductively heating said particles, wherein the time of treatment to effect said inductive heating under conditions to selectively alternate or kill the said cell population is correlated with the maximum responsiveness of particles in said cell population measured by the magnetic susceptibility of said particles.

7. The process of claim 6 including the further step of applying a localized, static field to aid in the intracellular uptake and energy absorption responsiveness of said particles, said field being applied after the provision of the particles to the host organism but prior to or during the application of said electromagnetic field.

8. The process according to claim 6 wherein the strength of said static field is between about 500 gauss and 80 kilogauss.

9. The process according to claim 6 wherein induction heating is continued to attain an increase in intracellular temperature of said cancer cells of between 8° C. and 100° C. to kill said cancer cells.

10. The process according to claim 6 wherein said induction heating is continued to attain an increase in intracellular temperature of at least 8.0° Centigrade and not greater than 9.5° Centigrade to kill said cancer cells.

11. A process for the treatment of cancer in at least one region of a host organism containing cancer cells and normal cells without substantially damaging living normal cells comprising:

providing to the host organism minute encapsulated tumoricidal material, said encapsulating material capable of being removed upon entering the cancer cell, determining after a period of metabolic time, the magnetic susceptibility of the particles with said region, subjecting the organism to an alternating, oscillating or pulsed electromagnetic field at that point in metabolic time when the maximum difference in magnetic susceptibility between the cancer cells and normal cells occurs thereby removing said encapsulating material and releasing said tumoricidal material within the cancer cells.

12. The method according to claim 11 wherein in response to said electromagnetic field said particle is inductively heated and said encapsulating material is melted.

13. The method according to claim 11 wherein in response to said electromagnetic field said particle vibrates thereby destroying the integrity of the encapsulating material.

14. The method according to claim 11 wherein said tumoricidal material is selected from the group consisting of antibodies, radioactive isotopes, and chemotherapeutic agents.

15. The method according to claim 14 wherein said chemotherapeutic agent is selected from the group consisting of 5-flurouracil, nitrogen mustard, actinomycin D, methotrexate, cytoxan and vincristine.

* * * * *